United States Patent
Harn et al.

(10) Patent No.: US 10,441,566 B2
(45) Date of Patent: Oct. 15, 2019

(54) USE OF BUTYLIDENEPHTHALIDE

(71) Applicant: EVERFRONT BIOTECH INC., New Taipei (TW)

(72) Inventors: Horng-Jyh Harn, Taipei (TW); Shinn-Zong Lin, Taichung (TW)

(73) Assignee: EVERFRONT BIOTECH INC., New Taipei (TW)

( * ) Notice: Subject to any disclaimer, the term of this patent is extended or adjusted under 35 U.S.C. 154(b) by 0 days.

(21) Appl. No.: 16/068,257

(22) PCT Filed: Jan. 7, 2016

(86) PCT No.: PCT/CN2016/070376
§ 371 (c)(1),
(2) Date: Jul. 5, 2018

(87) PCT Pub. No.: WO2017/117774
PCT Pub. Date: Jul. 13, 2017

(65) Prior Publication Data
US 2019/0008826 A1    Jan. 10, 2019

(51) Int. Cl.
*A61K 31/365*   (2006.01)
*A61K 9/08*     (2006.01)
*A61K 9/20*     (2006.01)
*A61P 35/00*    (2006.01)

(52) U.S. Cl.
CPC ............. *A61K 31/365* (2013.01); *A61K 9/08* (2013.01); *A61K 9/20* (2013.01); *A61P 35/00* (2018.01)

(58) Field of Classification Search
CPC .................................................. A61K 31/365
See application file for complete search history.

(56) References Cited

U.S. PATENT DOCUMENTS

2012/0208875 A1    8/2012   Lin et al.

FOREIGN PATENT DOCUMENTS

| CN | 104042606 | 9/2014 |
| TW | 201233392 | 8/2012 |

OTHER PUBLICATIONS

Rajendran (Bulletin of the World Health Organization, 1994, 72 (6): 985-996) (Year: 1994).*
Angadi et. al. (Oral Maxillofac Surg, 2011; 15:15-19) (Year: 2011).*
Yanjia, H. et al., "The role of epithelial-mesenchymal transition in oral squamous cell carcinoma and oral submucous fibrosis", Clinica Chimica Acta 383, 2007, pp. 51-56.

(Continued)

*Primary Examiner* — Marcos L Sznaidman
*Assistant Examiner* — Rayna Rodriguez
(74) *Attorney, Agent, or Firm* — Ping Wang; Morris, Manning & Martin, LLP

(57) ABSTRACT

Disclosed is the use of an active ingredient in the manufacture of a medicament, wherein the active ingredient is selected from the group consisting of butylidenephthalide (BP), a pharmaceutically acceptable salt of butylidenephthalide, and combinations thereof, and wherein the medicament is used for the prevention and/or treatment of oral submucous fibrosis (OSF) and may be used in the form of an injection lozenge, oral solution, or smearing preparation.

4 Claims, 5 Drawing Sheets

Specification includes a Sequence Listing.

(56) References Cited

OTHER PUBLICATIONS

Shukla, A. et al., "Oral Submucous Fibrosis: An Update on Etiology and Pathogenesis—A Review", Rama Univ J Dent Sci, 2015, vol. 2(1), pp. 24-33.

Tilakaratne, W. M. et al., "Oral submucous fibrosis: Review on aetiology and pathogenesis", Oral Oncology, 2006, vol. 42, pp. 561-568.

Rajalalitha, P. et al., "Molecular pathogenesis of oral submucous fibrosis—a collagen metabolic disorder", J Oral Pathol Med, 2005, vol. 34, pp. 321-328.

Moutasim, K. A. et al., "Betel-derived alkaloid up-regulates keratinocyte alphavbeta6 integrin expression and promotes oral submucous fibrosis", Journal of Pathology, 2011, vol. 223, pp. 366-377.

Chang, Y.C. et al., "Arecoline-induced myofibroblast transdifferentiation from human buccal mucosal fibroblasts is mediated by ZEB1", J. Cell. Mol. Med., vol. 18(4), 2014, pp. 698-708.

Yu, C.C. et al., "Elevation of S100A4 Expression in Buccal Mucosal Fibroblasts by Arecoline: Involvement in the Pathogenesis of Oral Submucous Fibrosis", PLOS ONE, 2013, vol. 8(1), pp. 1-8.

\* cited by examiner

```
                           SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Twist Primer - Forward sequence

<400> SEQUENCE: 1
gggagtccgc agtcttacga                                                    20

<210> SEQ ID NO 2
<211> LENGTH: 20
<212> TYPE: DNA
<213> ORGANISM: Artificial Sequence
<220> FEATURE:
<223> OTHER INFORMATION: Twist Primer - Reverse sequence

<400> SEQUENCE: 2
agaccgagaa ggcgtagctg                                                    20

<210> SEQ ID NO 3
<211> LENGTH: 20
<212> TYPE: DNA
<213> ORGANISM: Artificial Sequence
<220> FEATURE:
<223> OTHER INFORMATION: Snail Primer - Forward sequence

<400> SEQUENCE: 3
gcagctattt cagcctcctg                                                    20

<210> SEQ ID NO 4
<211> LENGTH: 20
<212> TYPE: DNA
<213> ORGANISM: Artificial Sequence
<220> FEATURE:
<223> OTHER INFORMATION: Snail Primer - Reverse sequence

<400> SEQUENCE: 4
gttctgggag acacatcggt                                                    20

<210> SEQ ID NO 5
<211> LENGTH: 23
<212> TYPE: DNA
<213> ORGANISM: Artificial Sequence
<220> FEATURE:
<223> OTHER INFORMATION: ZEB1 Primer - Forward sequence

<400> SEQUENCE: 5
agcagtgaaa gagaagggaa tgc                                                23

<210> SEQ ID NO 6
<211> LENGTH: 21
<212> TYPE: DNA
<213> ORGANISM: Artificial Sequence
<220> FEATURE:
<223> OTHER INFORMATION: ZEB1 Primer - Reverse sequence

<400> SEQUENCE: 6
ggtcctcttc aggtgcctca g                                                  21
```

```
<210> SEQ ID NO 7
<211> LENGTH: 24
<212> TYPE: DNA
<213> ORGANISM: Artificial Sequence
<220> FEATURE:
<223> OTHER INFORMATION: Alpha-SMA Primer - Forward sequence

<400> SEQUENCE: 7
agcacatgga aaagatctgg cacc                                          24

<210> SEQ ID NO 8
<211> LENGTH: 20
<212> TYPE: DNA
<213> ORGANISM: Artificial Sequence
<220> FEATURE:
<223> OTHER INFORMATION: Alpha-SMA Primer - Reverse sequence

<400> SEQUENCE: 8
ttttctcccg gttggccttg                                               20

<210> SEQ ID NO 9
<211> LENGTH: 17
<212> TYPE: DNA
<213> ORGANISM: Artificial Sequence
<220> FEATURE:
<223> OTHER INFORMATION: Col1a1 Primer - Forward sequence

<400> SEQUENCE: 9
gggtgaccgt ggtgaga                                                  17

<210> SEQ ID NO 10
<211> LENGTH: 19
<212> TYPE: DNA
<213> ORGANISM: Artificial Sequence
<220> FEATURE:
<223> OTHER INFORMATION: Col1a1 Primer - Reverse sequence

<400> SEQUENCE: 10
ccaggagagc cagaggtcc                                                19

<210> SEQ ID NO 11
<211> LENGTH: 18
<212> TYPE: DNA
<213> ORGANISM: Artificial Sequence
<220> FEATURE:
<223> OTHER INFORMATION: S100A4 Primer - Forward sequence

<400> SEQUENCE: 11
gagctgccca gcttcttg                                                 18

<210> SEQ ID NO 12
<211> LENGTH: 20
<212> TYPE: DNA
<213> ORGANISM: Artificial Sequence
<220> FEATURE:
<223> OTHER INFORMATION: S100A4 Primer - Reverse sequence

<400> SEQUENCE: 12
tgcaggacag gaagacacag                                               20
```

USE OF BUTYLIDENEPHTHALIDE

FIELD

The present invention relates to the use of butylidenephthalide in preventing and/or treating oral submucous fibrosis (OSF).

BACKGROUND

Oral submucous fibrosis is a pre-cancerous condition of oral cancer, but not an oral cancer. The primary features of oral submucous fibrosis are the inflammation and fibrosis of the oral submucosal tissue and deeper connective tissue. If the therapy for oral submucous fibrosis is not started immediately, the oral submucous fibrosis may develop into oral cancer.

There are epidemiological studies indicating that chewing *areca* nuts is the primary cause of oral submucous fibrosis. The lesions usually present in the buccal mucosa and secondarily present in the palatal portion and retromolar trigone. At first, the affected mucosa is blanched, and then, ulcers and blisters will appear repeatedly. Eventually, the mucosa will lose elasticity, and thus, may lead to a difficulty for patients to open their mouths wide that would seriously affect daily functions of mouths such as eating, teeth brushing, oral exams, and oral therapies. If the lesion occurs in the soft palate of oropharynx, it may cause dysphagia, uvula atrophy or uvula deformity. Patients of oral submucous fibrosis usually have a feeling of burning, stabbing pain and dryness, and are extremely sensitive to spicy and hot foods, but have a reduced gustatory sensation.

Currently, there is no drug that can prevent and/or treat oral submucous fibrosis effectively. Therapies of oral submucous fibrosis usually rely on the steroid injections to reduce the content of collagen in the oral submucosal tissue, or rely on the traditional surgery or laser surgery to excise the affected tissues. However, steroid injections can only alleviate the symptoms and cannot cure the oral submucous fibrosis. There are side effects such as moon face, obesity, buffalo hump, osteoporosis, skin thinning, edema, susceptibility to infection, acne, retardation of height, increased blood sugar, increased infection rate, oral fungal infection, increased body hair and impaired wound healing. Furthermore, the excision of a large tissue lesion via traditional surgery or laser surgery may easily lead to wound contraction and scar formation during wound healing, and thus needs to take the issues such as the limitations of opening mouths and facial appearance into consideration. In this respect, oral surgeons would consider skin grafts as the remedial measure, but the skin grafts may hide early relapses. In addition, as treating older patients or patients having large lesions with traditional surgery or laser surgery, both the surgical damages and patients' immunity and life quality will be considered.

In view of the above issues regarding the therapies of oral submucous fibrosis, pharmaceutical researchers are dedicated to developing drugs which can prevent and/or treat oral submucous fibrosis. Inventors of the present invention discovered that butylidenephthalide is effective in inhibiting the epithelial-mesenchymal transition (EMT) of oral submucosal tissue cells, inhibiting oral submucosal tissue cells to differentiate into myofibroblasts, and inhibiting the activation of myofibroblasts, and thus, can inhibit the accumulation of collagen in oral submucosal tissue, inhibit the contraction of extracellular matrix in oral submucosal tissue, and be used to provide drugs that can prevent and/or treat oral submucous fibrosis.

SUMMARY

An objective of the present invention is to provide a use of an active ingredient in the manufacture of a medicament, wherein the active ingredient is selected from the group consisting of butylidenephthalide (BP), a pharmaceutical acceptable salt of butylidenephthalide, and combinations thereof. The medicament is used for preventing and/or treating oral submucous fibrosis (OSF). Preferably, the medicament is used as an injection, a tablet, an oral liquid, or a smearing preparation.

Another objective of the present invention is to provide a pharmaceutical composition, which is used for preventing and/or treating oral submucous fibrosis (OSF) and comprises an effective amount of an active ingredient and a pharmaceutical acceptable carrier, wherein the active ingredient is selected from the group consisting of butylidenephthalide (BP), a pharmaceutical acceptable salt of butylidenephthalide, and combinations thereof. Preferably, the pharmaceutical composition is used as an injection, a tablet, an oral liquid, or a smearing preparation.

Still another objective of the present invention is to provide a method for preventing and/or treating oral submucous fibrosis (OSF), comprising administering to a subject in need an effective amount of an active ingredient, wherein the active ingredient is selected from the group consisting of butylidenephthalide (BP), a pharmaceutical acceptable salt of butylidenephthalide, and combinations thereof. Furthermore, the active ingredient can be administered to a subject in a form of an injection, a tablet, an oral liquid, or a smearing preparation.

The detailed technology and some of the embodiments implemented for the present invention are described in the following paragraphs for persons skilled in the art to well appreciate the features of the claimed invention.

BRIEF DESCRIPTION OF THE DRAWINGS

FIGS. 2A and 2B are histograms showing the relative expression levels (fold) of the Twist gene, Snail gene, and ZEB1 gene in fBMF-1 or fBMF-2 that are treated with different concentrations of butylidenephthalide (BP), wherein the relative expression level of gene is analyzed by a quantitative real-time polymerase chain reaction (Q-PCR), and wherein, FIG. 2A shows the results of fBMF-1 and FIG. 2B shows the results of fBMF-2;

FIGS. 4A and 4B are histograms showing the relative expression levels (fold) of α-SMA gene, Col1a1 gene, and S100A4 gene in fBMF-1 or fBMF-2 that are treated with different concentrations of butylidenephthalide (BP), wherein the relative expression level of gene is analyzed by Q-PCR, and wherein, FIG. 4A shows the results of fBMF-1 and FIG. 4B shows the results of fBMF-2;

DETAILED DESCRIPTION

Figure 1:
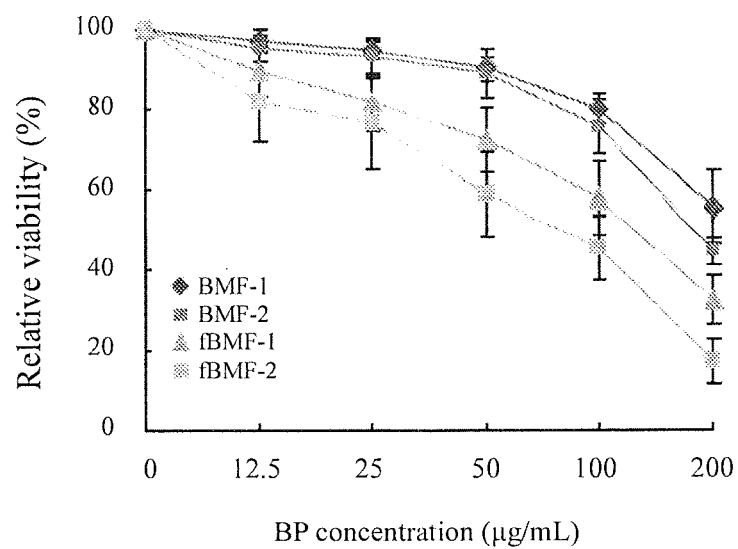
FIG. 1 is a curve diagram showing the relative viability (%) of buccal mucosal fibroblasts (BMFs; including "BMF-1 (i.e., ◆)" and "BMF-2 (i.e., ※)") that are treated with different concentrations of butylidenephthalide (BP) and that of fibrotic buccal mucosal fibroblasts (fBMFs; including "fBMF-1 (i.e., ▲)" and "fBMF-2 (i.e., ▨)") that are treated with different concentrations of butylidenephthalide (BP)

The following paragraphs will describe some of the embodiments of the present invention in detail. However, without departing from the spirit of the present invention, the present invention may be embodied in various embodiments and should not be limited to the embodiments described in the specification and the appended claims. Unless otherwise indicated herein, the expression "a," "an," "the," or the like recited in the specification of the present invention (especially in the claims) are intended to include both the singular and plural forms. In addition, the word "about" as used herein substantially represents values within ±20% of the stated value, preferably within ±10%, and more preferably within ±5%.

In the specification, the terms "prevention", "prevent", "preventing", "preventive", and "prophylaxix" refer to avoiding or minimizing the onset or deterioration of diseases or symptoms, or reducing the morbidity rate or deterioration speed of diseases or symptoms; the terms "treatment", "treat", and "treating" refer to the eradication, removal, reversal, mitigation, alleviation, or control of a disease or a symptom; the term "an effective amount" refer to the amount of the substance that can at least partially alleviate the illness of a suspected subject when the substance is administered to the subject; the term "subject" refers to a mammalian, and the mammalian can be a human or non-human animal.

It has been proved by researches that during the process of oral submucous fibrosis, the oral submucosal tissue cells would carry out an epithelial-mesenchymal transition (EMT) and differentiate into myofibroblasts. Furthermore, when cells carry out an EMT, the Twist gene, Snail gene, and ZEB1 gene would highly express in cells, while the intercellular polarity would sequentially lose and the migration ability of cells would be enhanced such that the cells could crawl and invade easily and then participate in the fibrosis of tissue. Myofibroblasts are cells that can express marker genes such as α-SMA gene, Col1a1 gene, and S100A4 gene, and have a high mobility. The activated myofibroblasts secrete excessive extracellular matrix (ECM) such as fibronectin and collagen, and thus, may induce the contraction of extracellular matrix of tissue cells, thereby, promoting the fibrosis of tissue. It has also been proved that the excessive accumulation of extracellular matrix is closely associated with the occurrence of oral submucous fibrosis. The aforementioned facts can be noted from papers such as "The role of epithelial-mesenchymal transition in oral squamous cell carcinoma and oral submucous fibrosis. *Clin Chim Acta*. August; 383(1-2): 51-56 (2007)", "Oral submucous fibrosis: An update on etiology and pathogenesis-A review. *Rama Univ J Dent Sci*. March; 2(1): 24-33 (2015)", "Oral submucous fibrosis: Review on aetiology and pathogenesis. *Oral Oncol*. July; 42(6):561-568 (2006)", and "Molecular pathogenesis of oral submucous fibrosis—a collagen metabolic disorder. *J Oral Pathol Med*. July; 34(6): 321-328 (2005)", which are entirely incorporated hereinto by reference.

Since the EMT of tissue cells and the activation of myofibroblasts are closely associated with oral submucous fibrosis, it is believed that if the EMT of oral submucosal tissue cells, differentiation of oral submucosal tissue cells into myofibroblasts, and/or activation of myofibroblasts can be inhibited, the excessive accumulation of extracellular matrix and the contraction of extracellular matrix in tissue will be effectively inhibited. Thus, the oral submucous fibrosis can be prevented and/or treated. The aforementioned facts can be noted from papers such as "Betal-drived alkaloid up-regulates keratinocyte alphavbeta6 integrin expression and promotes oral submucous fibrosis. *J Pathol*. February; 223(3): 366-377 (2011)", "Arecoline-induced myofibroblast transdifferentiation from human buccal mucosal fibroblasts is mediated by ZEB1. *J Cell Mol Med*. April; 18(4): 698-708 (2014)", and "Elevation of S100A4 expression in buccal mucosal fibroblasts by arecoline: involvement in the pathogenesis of oral submucous fibrosis. *PLoS One*. 8(1): e55122 (2013)", which are entirely incorporated hereinto by reference.

Inventors of the present invention discovered that treating the cells of fibrotic oral submucosal tissues with butylidenephthalide (BP) can effectively inhibit the EMT of the cells, and especially can inhibit the expressions of the Twist gene, Snail gene, and ZEB1 gene in the cells and inhibit the cells from crawling and invading. Accordingly, an effect of inhibiting oral submucous fibrosis can be provided.

Inventors of the present invention also discovered that treating the cells of fibrotic oral submucosal tissues with butylidenephthalide (BP) can effectively inhibit the cell differentiate into myofibroblasts and inhibit the activation of myofibroblasts, and especially can inhibit the expressions of α-SMA gene, Col1a1 gene, and S100A4 gene in the cells and inhibit the contraction of extracellular matrix in tissues. Accordingly, an effect of inhibiting oral submucous fibrosis can be provided.

Therefore, the present invention provides a medicament, a pharmaceutical composition, and a method for preventing and/or treating oral submucous fibrosis, wherein the medicament is manufactured by using an active ingredient, the pharmaceutical composition comprises an effective amount of an active ingredient and a pharmaceutical acceptable carrier, and the method comprises administering to a subject in need an effective amount of an active ingredient. In the medicament, pharmaceutical composition, and method in accordance with the present invention, the active ingredient is selected from the group consisting of butylidenephthalide (BP), a pharmaceutically acceptable salt of butylidenephthalide, and combinations thereof.

In the medicament, pharmaceutical composition, and method of the present invention, the examples of pharmaceutical acceptable carrier include alkali metal salts, such as sodium salts and potassium salts; alkaline earth metal salts, such as calcium salts, magnesium salts, and barium salts; transition metal salts, such as zinc salts, copper salts, ferric salts, cobalt salts, titanium salts, vanadium salts; aluminium salts; stannum salts; alkanolamine salts, such as diethanolamine salts, 2-amino-2-ethyl-1,3-propanediol salts, and triethanolamine salts; heterocyclic amine salts, such as morpholine salts, piperazine salts, and piperidine salts; and alkali amine salts, such as amine salts, arginine salts, lysine salts and histidine salts, but is not limited thereby. Preferably, the active ingredient used in the medicament, pharmaceutical composition, and method of the present invention is butylidenephthalide (BP).

When the medicament or pharmaceutical composition of the present invention is used for preventing and/or treating oral submucous fibrosis, the medicament or pharmaceutical composition can present in any suitable form depending on the desired purpose. For example, the medicament or pharmaceutical composition can be administered to a subject in need by intracutaneous, intramuscular, intraperitoneal, intravenous, subcutaneous, oral, percutaneous and mucous routes, but is not limited thereby.

As a dosage form suitable for the intracutaneous, intramuscular, intraperitoneal, intravenous and subcutaneous administrations, the medicament or pharmaceutical composition of the present invention can be provided as an injection, but does not be limited thereby. Examples of injections include an intravenous infusion, an emulsified intravenous infusion, a powder for injection, a suspension for injection, and a powder suspension for injection, but is not limited thereby. Alternatively, the medicament or pharmaceutical composition can be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

As a dosage form suitable for oral administration, the medicament or pharmaceutical composition of the present invention can be provided in a solid form such as a tablet, a pill, a capsule, granules, and a pulvis, or a liquid form such as an oral liquid, a syrup, a spirit, an elixir, and a tincture, but is not limited thereby.

As a dosage form suitable for percutaneous or mucous administrations, the medicament or pharmaceutical composition of the present invention can be provided in the form of swab, such as a lotion, a cream, a gel (a hydrogel), a paste (a dispersed paste and an ointment), a mouthwash, a washing agent, a spray, or a patch preparation (patch), but is not limited thereby.

Preferably, the medicament and pharmaceutical composition of the present invention is provided as an injection, a tablet, an oral liquid, or a smearing preparation.

In the present invention, depending on the route and/or the form of the administration, a suitable pharmaceutical acceptable carrier can be chosen to provide the medicament of the present invention. In addition, the pharmaceutical composition of the present invention can also comprise a pharmaceutical acceptable carrier. Examples of the pharmaceutical acceptable carrier include, but are not limited to, solvents (buffer, water, saline, dextrose, glycerol, ethanol or its analogs, and combinations thereof), oily solvents, diluents, stabilizers, absorbent retarders, disintegrating agents, emulsifiers, antioxidants, adhesives, binders, tackifiers, hydrotropic agents, dispersants, suspending agents, lubricants, hygroscopic agents, solid carriers (e.g., starch and bentonite).

Optionally, the medicament or pharmaceutical composition of the present invention can be packaged into a drug delivery system such as liposome, microparticle, or microcapsule, and then be administered to a subject in need to enhance the delivery efficiency of active ingredients in the medicament or pharmaceutical composition, as long as the components of the drug delivery system will not adversely affect the desired effects of the active ingredients of the present invention (i.e., butylidenephthalide (BP), a pharmaceutically acceptable salt of butylidenephthalide, or combinations thereof).

Optionally, the medicament or pharmaceutical composition of the present invention can further comprise a suitable amount of additives, such as a flavoring agent (e.g., sucrose), a toner, or a coloring agent for enhancing the palatability and the visual perception of the medicament or pharmaceutical composition, and a buffer, a conservative, a preservative, an antibacterial agent, or an antifungal agent for improving the stability and storability of the medicament or pharmaceutical composition. In addition, the medicament or pharmaceutical composition can optionally comprise one or more other active ingredient(s) (e.g., steroids), or to be used in combination with a medicament comprising one or more other active ingredient(s), to further enhance the effects of the medicament or pharmaceutical composition, or to increase the application flexibility and application adaptability of the preparation thus provided, as long as the other active ingredients will not adversely affect the desired effects of the active ingredients of the present invention (i.e., butylidenephthalide (BP), a pharmaceutically acceptable salt of butylidenephthalide, or combinations thereof).

Depending on the age, body weight, and health conditions of the subject, the medicament or pharmaceutical composition provided by the present invention can be administered at various frequencies, such as once a day, multiple times a day, or once every few days, etc. For example, when the medicament or pharmaceutical composition is administered orally to a subject to prevent and/or treat oral submucous fibrosis, the dosage of the medicament or pharmaceutical composition is about 5 mg (as BP)/kg body weight to about 500 mg (as BP)/kg body weight per day, preferably is about 10 mg (as BP)/kg body weight to about 120 mg (as BP)/kg body weight per day, and more preferably is about 20 mg (as BP)/kg body weight to about 90 mg (as BP)/kg body weight per day, wherein the unit "mg/kg body weight" refers to the dosage required per kilogram of body weight of the subject. However, for acute patients, the dosage can be optionally increased up to several folds or dozen folds, depending on the requirements of the practical application.

In addition, the medicament or pharmaceutical composition provided in accordance with the present invention can be also used in a combination with one of the following operations to prevent and/or treat oral submucous fibrosis: traditional surgery and laser surgery.

In the method for preventing and/or treating oral submucous fibrosis in accordance with the present invention, the administered route, administered form, suitable dosage, and related uses in therapeutic applications of the active ingredients (i.e., butylidenephthalide (BP), a pharmaceutically acceptable salt of butylidenephthalide, or combinations thereof) are all in line with the above descriptions.

The present invention will be further illustrated in detail with specific examples as follows. However, the following examples are provided only for illustrating the present invention. The scope of the present invention is not limited thereby and will be indicated in the appended claims.

EXAMPLES

Preparation Examples

A. Cell Cultivation

Two groups of buccal mucosal fibroblasts obtained from normal oral buccal mucosa (hereinafter abbreviated as "BMF-1" and "BMF-2"; or collectively called "BMFs"), and two groups of fibrotic buccal mucosal fibroblasts obtained from fibrotic oral buccal mucosa (hereinafter abbreviated as "fBMF-1" and "fBMF-2"; or collectively called "fBMFs") were respectively subjected to the following procedures: seeding the cells into a 24-well plate by a concentration of 2×10⁴ cells/well to cultivate the cells to reach a 80% confluence, and then respectively treating the cells with different concentrations (0, 12.5, 25, 50, 100, or 200 μg/mL) of butylidenephthalide (BP) for 48 hours.

B. Extraction of Total RNA from Cells

The cells of each group provided by [Preparation example A] were suspended by trypsin and then respectively subjected to the following procedures: (i) conducting a centrifugation (1000 rpm, 5 minutes) and removing the supernatant; (ii) mixing the supernatant with 1 mL of TRIzol reagent (purchased from Invitrogen Life Technologies) evenly, and then keeping the mixture thus obtained at room temperature for 5 minutes; (iii) mixing the product of step (ii) with 100 μL of BCP (bromochloropropane), then shaking the mixture thus provided evenly, and keeping the same at room temperature for 5 minutes; (iv) subjecting the product of step (iii) to a centrifugation (Eppendorf centrifuge, F45-30-11 rotor, 4□, 12000 rpm, 15 minutes), then moving the upper liquid into a new eppendorf, mixing the same with isopropanol evenly, and keeping the mixture thus obtained at room temperature for 5 minutes; (v) subjecting the product of step (iv) to a centrifugation (Eppendorf centrifuge, F45-30-1 rotor, 4□, 12000 rpm, 10 minutes), then removing the supernatant and washing the RNA precipitated in the bottom of the eppendorf with 500 μL of 75% ethanol; (vi) conducting a centrifugation (room temperature, 12000 rpm, 5 minutes) to remove the ethanol layer, and then placing the eppendorf in a fume hood to dry the RNA precipitate; and (vii) dissolving the RNA precipitate with 20 μL of diethyl pyrocarbonate (DEPC)-treated water, and then measuring the absorbance value of the mixture thus obtained at a wavelength of 260 nm to calculate the RNA concentration.

Example 1: Evaluation of Cytotoxicity of Butylidenephthalide (BP)

The cells of each group provided by [Preparation example A] were respectively subjected to the following procedures: (i) removing the supernatant in the 24-well plate, and then adding 500 μL of 3-(4,5-dimethylthiazol-2-yl)-2,5-diphenyl tetrazolium bromide (abbreviated as "MTT") buffer into each well (the final concentration of MTT is 0.5 mg/mL); (ii) placing the plate in an incubator at 37□ and 5% $CO_2$ for 3 hours; (iii) removing the supernatant, and then respectively adding 1000 μL of isopropanol into each well, and placing the plate on a shaker to shake for 10 minutes; and (iv) moving 200 μL solution from each well into a 96-well plate, and then measuring the absorbance value of the same at a wavelength of 570 nm by using a spectrophotometer to calculate the relative viability (%) of the cells in each group. The results are shown in FIG. 1.

As shown in FIG. 1, if the buccal mucosal fibroblasts (BMFs) and fibrotic buccal mucosal fibroblasts (fBMFs) are cultivated in a medium externally added with butylidenephthalide (BP) at a concentration of no more than 50 μg/mL, their growth will not be affected. Therefore, the following experiments were conducted with the use of butylidenephthalide (BP) at a concentration ranging from 0 to 50 μg/mL.

Example 2: Analysis of the Effects of Butylidenephthalide (BP) in Inhibiting Epithelial-Mesenchymal Transition (EMT) of Oral Submucosal Tissue Cells A. Expression of Marker Genes in Epithelial-Mesenchymal Transition (EMT)

It is known that during the process of epithelial-mesenchymal transition (EMT), the expressions of Twist gene, Snail gene, and ZEB1 gene in the cells will increase, and thus, these genes are known as the marker genes of EMT. In this experiment, quantitative real-time polymerase chain reaction (Q-PCR) was conducted to investigate whether butylidenephthalide (BP) can affect the expressions of Twist gene, Snail gene, and ZEB1 gene in oral submucosal tissue cells.

First, 1 μg total RNAs of each group provided by [Preparation example B] was subjected to a reverse transcription to provide complementary DNA (cDNA). Thereafter, the cDNA was subjected to Q-PCR by using a gene quantitation system (PRISM ABI7700 Sequence Detecting System; purchased from America Applied Biosystems company) and specific primers (as shown in Table 1) to analyze the expressions of Twist gene, Snail gene, and ZEB1 gene in fBMFs (including fBMF-1 and fBMF-2) that are treated with different concentrations of butylidenephthalide (BP) (0, 25, or 50 μg/mL). Finally, the relative gene expression levels (fold) of each group were calculated by using the gene expression level of the group that are not treated with butylidenephthalide (BP) as a basis. The results are shown in FIG. 2.

TABLE 1

| | retro-transcription | |
|---|---|---|
| Gene name | Nucleotide sequence of primers | Sequence number |
| Twist | (forward primer) GGGAGTCCGCAGTCTTACGA | SEQ ID NO: 1 |
| | (reverse primer) AGACCGAGAAGGCGTAGCTG | SEQ ID NO: 2 |
| Snail | (forward primer) GCAGCTATTTCAGCCTCCTG | SEQ ID NO: 3 |
| | (reverse primer) GTTCTGGGAGACACATCGGT | SEQ ID NO: 4 |
| ZEB1 | (forward primer) AGCAGTGAAAGAGAAGGGAATGC | SEQ ID NO: 5 |
| | (reverse primer) GGTCCTCTTCAGGTGCCTCAG | SEQ ID NO: 6 |

Figure 2A:
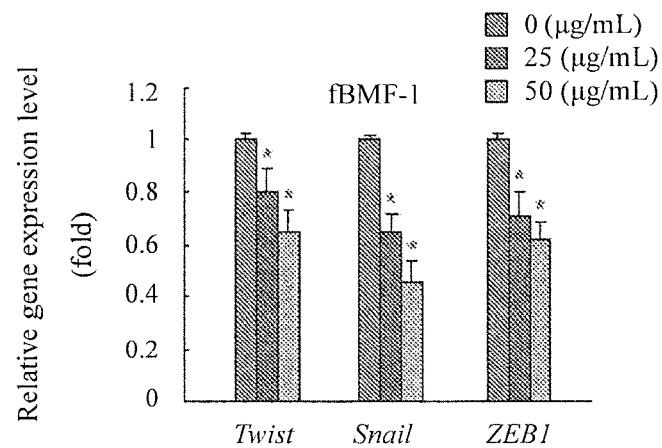
Figure 2B:
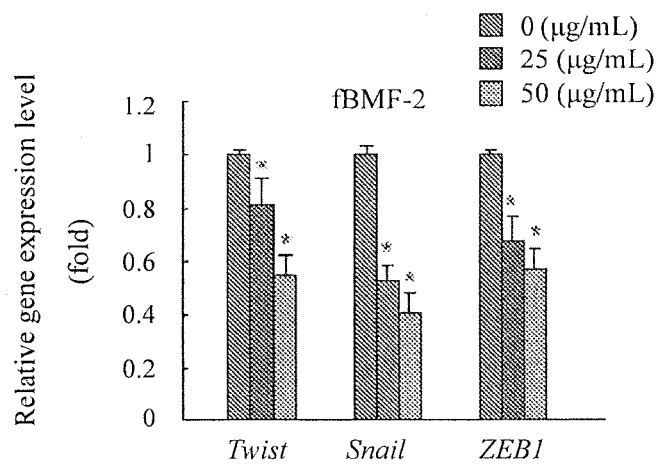

As shown in FIG. 2, no matter in fBMF-1 or fBMF-2, the expressions of Twist gene, Snail gene, and ZEB1 gene all significantly decreased with the increment in the concentration of butylidenephthalide (BP). The above results indicate that butylidenephthalide (BP) is effective in inhibiting the epithelial-mesenchymal transition (EMT) of oral submucosal tissue cells, and thus, can be used for preventing and/or treating oral submucous fibrosis.

B. Abilities of Oral Submucosal Tissue Cells to Crawl and Invade

In this experiment, a transwell cell migration assay system (Transwell® system; purchased from Corning company, UK) and a polycarbonate membrane with a pore size of 8 μm (purchased from Corning company, UK) were used to further investigate whether butylidenephthalide (BP) can inhibit the abilities of oral submucosal tissue cells to crawl and invade.

First, the cell medium containing 10% FBS (fetal bovine serum) was added into the lower chamber, and an apparatus of polycarbonate membrane was placed on the bottom of a cell culture plate, i.e., upper chamber. On the other hand, the BMF-1, BMF-2, fBMF-1, and fBMF-2 provided by [Preparation example A] (2×10⁴ cells/group) were evenly mixed with a 250 μL serum-free medium that is externally added with butylidenephthalide (BP) by a concentration of 0, 25, or 50 μg/mL. Then, the mixtures thus obtained were respectively added into the upper chambers. Thereafter, the whole transwell cell migration assay system was placed in an incubator to induce cell migration for 24 hours. The transwell cell migration assay system was moved out from the incubator, and the cells on the polycarbonate membrane which do not migrate from the upper chamber to the lower chamber were removed. Then, the polycarbonate membrane were fixed with 4% paraformaldehyde for 10 minutes and stained with 0.1% crystal violet. Finally, the polycarbonate membranes were carefully cut and put on the microscope slide to be observed via a microscope under an amplification of 100 fold (the membrane of each group were observed in five different visual fields) and photographed. The cell numbers on the membrane were calculated into the relative cell migration ability (%) by using the results of BMFs not treated with butylidenephthalide (BP) as a basis. The above experiment was repeated thrice and the results are shown in FIGS. 3A and 3B, wherein the dark parts-in FIG. 3A are cells which migrated from the upper chamber to the lower chamber, and FIG. 3B shows the relative cell migration ability (%) obtained by averaging the results of the three repeated experiments.

Figure 3A:
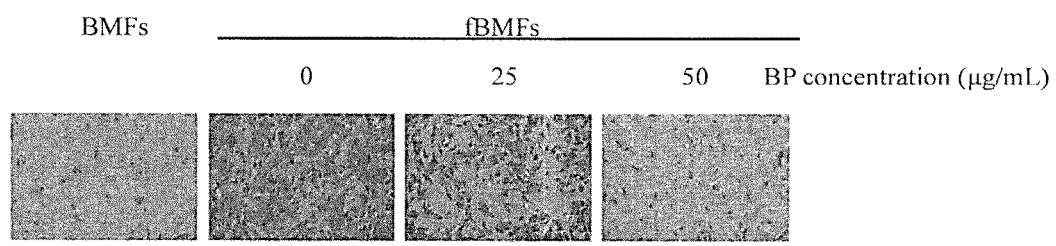
FIG. 3A is a photograph showing the migration of BMFs and fBMFs that is treated with different concentrations of butylidenephthalide (BP) from the upper chamber to the lower chamber, wherein the darkparts are cells.
Figure 3B:
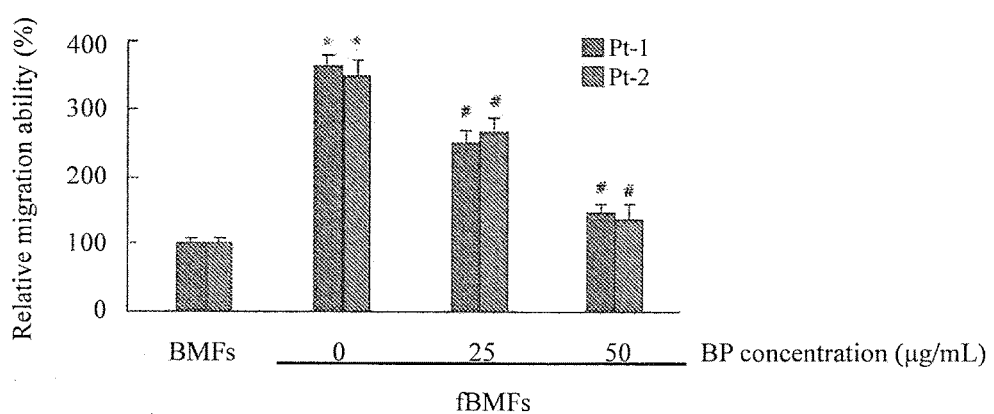
FIG. 3B is a histogram showing the relative migration ability (%) of BMFs (including BMF-1 (i.e., ▨) and BMF-2 (i.e., ▨)), and fBMFs (including fBMF-1 (i.e., ▨) and fBMF-2 (i.e., ▨) that are treated with different concentrations of butylidenephthalide (BP)

As shown in FIGS. 3A and 3B, in comparison with "BMFs group", the cells which migrated from the upper chamber to the lower chamber in "fBMFs group" are significantly increased. However, in the "fBMFs group", if cells were pre-treated with butylidenephthalide (BP), the cells which migrated from the upper chamber to the lower chamber would decrease with the increment in the concentration of butylidenephthalide (BP). These results indicate that in comparison with the normal oral submucosal tissue cells, the cells of fibrotic oral submucosal tissues have better abilities to crawl and invade, and thus, can perform an epithelial-mesenchymal transition (EMT) easily. And, butylidenephthalide (BP) is effective in inhibiting the abilities of oral submucosal tissue cells to crawl and invade. That is, butylidenephthalide (BP) is effective in inhibiting the epithelial-mesenchymal transition (EMT) of oral submucosal tissue cells, and thus, can be used for preventing and/or treating oral submucous fibrosis.

Example 3: Analysis of the Effects of Butylidenephthalide (BP) in Inhibiting Oral Submucosal Tissue Cells to Differentiate into Myofibroblasts It is known that during the process of the fibrosis of tissue, the tissue cells would differentiate and become myofibroblasts, wherein the α-SMA gene, Col1a1 gene, and S100A4 gene are the maker genes of myofibroblasts. Thus, in this experiment, a quantitative real-time polymerase chain reaction (Q-PCR) was conducted to investigate whether butylidenephthalide (BP) can inhibit the expressions of α-SMA gene, Col1a1 gene, and S100A4 gene in oral submucosal tissue cells.

1 μg total RNAs of each group provided by [Preparation example B] was subjected to reverse transcription to provide complementary DNA (cDNA). Thereafter, the cDNA was subjected to Q-PCR by using a gene quantitation system (PRISM ABI7700 Sequence Detecting System; purchased from America Applied Biosystems company) and specific primers (as shown in Table 2) to analyze the expressions of α-SMA gene, Col1a1 gene, and S100A4 gene in fBMFs (including fBMF-1 and fBMF-2) that are treated with different concentrations of butylidenephthalide (BP) (0, 25, or 50 μg/mL). Finally, the relative gene expression levels (fold) of each group were calculated by using the gene expression level of the group that are treated with butylidenephthalide (BP) as a basis. The results are shown in FIG. 4.

TABLE 2

| retro-transcription | | |
|---|---|---|
| Gene name | Nucleotide sequence of primers | Sequence number |
| α-SMA | (forward primer) AGCACATGGAAAAGATCTGGCACC | SEQ ID NO: 7 |
| | (reverse primer) TTTTCTCCCGGTTGGCCTTG | SEQ ID NO: 8 |
| Col1a1 | (forward primer) GGGTGACCGTGGTGAGA | SEQ ID NO: 9 |
| | (reverse primer) CCAGGAGAGCCAGAGGTCC | SEQ ID NO: 10 |
| S100A4 | (forward primer) GAGCTGCCCAGCTTCTTG | SEQ ID NO: 11 |
| | (reverse primer) TGCAGGACAGGAAGACACAG | SEQ ID NO: 12 |

Figure 4A:
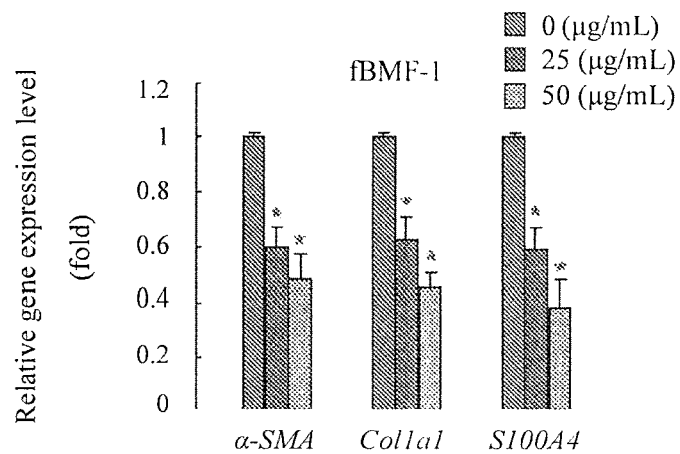
Figure 4B:
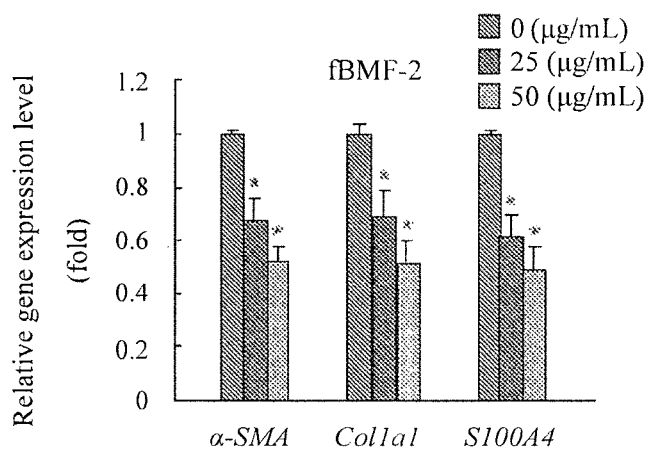

As shown in FIG. 4, no matter in fBMF-1 or fBMF-2, the expressions of α-SMA gene, Col1a1 gene, and S100A4 gene significantly decreased with the increment in the concentration of butylidenephthalide (BP). The above results indicate the butylidenephthalide (BP) is effective in inhibiting oral submucosal tissue cells to differentiate into myofibroblasts, and thus, can be used for inhibiting the accumulation of collagen in oral submucosal tissue, thereby effectively preventing and/or treating oral submucous fibrosis.

Example 4: Analysis of the Effects of Butylidenephthalide (BP) in Inhibiting the Contraction of Extracellular Matrix in Oral Submucous Tissue Cells The BMF-1, BMF-2, fBMF-1, and fBMF-2 provided by [Preparation example A] were respectively dissolved in 0.5 mL of 2 mg/mL collagen solution (purchased from Sigma-Aldrich), and the mixtures thus obtained were moved into a 24-well plate. Then, the 24-well plate was placed in an incubator at 370 and 5% $CO_2$ for 2 hours to coagulate the collagen gels. The gels thus obtained were respectively called "BMFs group", and "fBMFs group" gels. Thereafter, the coagulated gels were disengaged from the culture plate, and 0.5 mL of a medium containing different concentrations (0, 25, or 50 μg/mL) of butylidenephthalide (BP) was added thereinto to incubate with the gels for 48 hours. The contraction of gel in each group were observed and photographed. Finally, the relative gel area (%) of each "fBMFs group" was calculated by using the image-analyzed software, ImageJ (National Institutes of Health, USA) and using the results of "BMFs group" not being treated with butylidenephthalide (BP) as a basis. The results are shown in FIGS. 5A and 5B, wherein FIG. 5A shows the gel contraction induced by the cells of each group, and FIG. 5B shows the relative gel area (%) of each group.

Figure 5A:
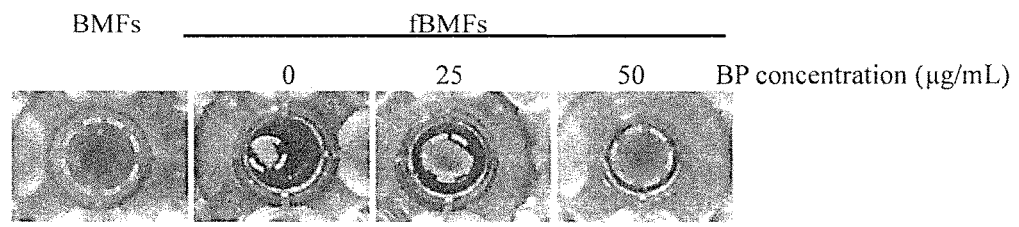
FIG. 5A is a photograph showing the gel contractions of fBMFs that are treated with different concentrations of butylidenephthalide (BP), wherein the area circled by the green dotted line is the gel.
Figure 5B:
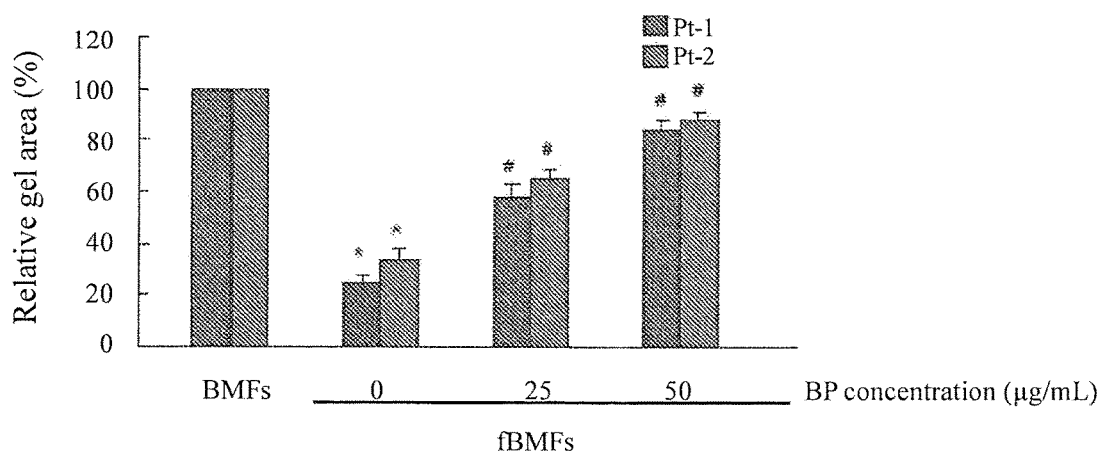
FIG. 5B is a histogram showing the relative gel area (%) after the gel contraction is induced by BMFs (including BMF-1 (i.e., ▨) and BMF-2 (i.e., ▨)) and that after the gel contraction induced by fBMFs (including fBMF-1 (i.e., ▨) and fBMF-2 (i.e., ▨) that are treated with different concentrations of butylidenephthalide (BP).

As shown in FIGS. 5A and 5B, in comparison with "BMFs group", the gel area of "fBMFs group" is significantly less, i.e., the gel was significantly contracted. However, in "fBMFs group", if the cells in gel were pre-treated with butylidenephthalide (BP), the gel contraction would significantly mitigate with the increment in the concentration of butylidenephthalide (BP). These results indicate that butylidenephthalide (BP) is effective in inhibiting the activation of myofibroblasts, thereby inhibiting the contraction of extracellular matrix in oral submucosal tissues.

Given the above experimental results, butylidenephthalide (BP) can effectively inhibit the epithelial-mesenchymal transition (EMT) of oral submucosal tissue cells, inhibit oral submucosal tissue cells to differentiate into myofibroblasts, and inhibit the activation of myofibroblasts, and thus, can inhibit the accumulation of collagen in oral submucosal tissue and inhibit the contraction of extracellular matrix in oral submucosal tissues.

What is claimed is:

1. A method for treating oral submucous fibrosis (OSF), comprising administering to a subject in need an effective amount of an active ingredient, wherein the active ingredient is selected from the group consisting of butylidenephthalide (BP), a pharmaceutically acceptable salt of butylidenephthalide, and combinations thereof.

2. The method as claimed in claim 1, wherein the active ingredient is administered as an injection, a tablet, an oral liquid, or a smearing preparation.

3. A method for treating oral submucous fibrosis (OSF), comprising administering to a subject in need an effective amount of an active ingredient, wherein the active ingredient is selected from the group consisting of butylidenephthalide (BP), a pharmaceutically acceptable salt of butylidenephthalide, and combinations thereof, wherein the method is for at least one of inhibiting epithelial-mesenchymal transition (EMT) of oral submucosal tissue cells, inhibiting the abilities of oral submucosal tissue cells to crawl and invade, inhibiting oral submucosal tissue cells to differentiate into myofibroblasts, inhibiting the activation of myofibroblasts, and inhibiting the contraction of extracellular matrix in oral submucosal tissues.

4. The method as claimed in claim 3, wherein the active ingredient is administered as an injection, a tablet, an oral liquid, or a smearing preparation.

\* \* \* \* \*